US010758000B2

(12) United States Patent
Naiker

(10) Patent No.: US 10,758,000 B2
(45) Date of Patent: Sep. 1, 2020

(54) FOOTWEAR HAVING MULTIPLE MASSAGE DEVICES AND METHOD

(71) Applicant: Rohit Sanjivan Naiker, Surrey (CA)

(72) Inventor: Rohit Sanjivan Naiker, Surrey (CA)

( * ) Notice: Subject to any disclaimer, the term of this patent is extended or adjusted under 35 U.S.C. 154(b) by 60 days.

(21) Appl. No.: 16/050,184

(22) Filed: Jul. 31, 2018

(65) Prior Publication Data

US 2020/0037700 A1 Feb. 6, 2020

(51) Int. Cl.

| | |
|---|---|
| ***A61F 5/14*** | (2006.01) |
| ***A43B 7/14*** | (2006.01) |
| ***A43B 7/02*** | (2006.01) |
| ***A43B 7/04*** | (2006.01) |
| ***A43B 17/02*** | (2006.01) |
| ***A43B 3/00*** | (2006.01) |
| ***A61H 7/00*** | (2006.01) |
| *A43C 11/14* | (2006.01) |

(52) U.S. Cl.

CPC ............ *A43B 7/146* (2013.01); *A43B 3/0005* (2013.01); *A43B 7/02* (2013.01); *A43B 7/04* (2013.01); *A43B 17/02* (2013.01); *A61H 7/004* (2013.01); *A43C 11/1493* (2013.01); *A61H 2201/0228* (2013.01); *A61H 2201/123* (2013.01); *A61H 2201/165* (2013.01); *A61H 2201/1645* (2013.01); *A61H 2201/1664* (2013.01); *A61H 2201/501* (2013.01)

(58) Field of Classification Search

CPC .............................. A43B 7/146; A43B 3/0005
USPC ............................................................ 36/141
See application file for complete search history.

(56) References Cited

U.S. PATENT DOCUMENTS

| | | | | | |
|---|---|---|---|---|---|
| 5,681,266 | A * | 10/1997 | Lin | A61H 23/006 | 601/101 |
| 5,682,690 | A * | 11/1997 | Chang | A43B 7/00 | 36/11.5 |
| 8,632,481 | B2 | 1/2014 | Shi | | |
| 9,730,853 | B2 * | 8/2017 | Tassin | A61H 1/008 | |
| 2006/0235465 | A1 * | 10/2006 | Koo | A43B 1/0054 | 606/204 |
| 2012/0186101 | A1 * | 7/2012 | Sanchez | A43B 3/0005 | 36/44 |
| 2012/0260531 | A1 * | 10/2012 | Shi | A43B 3/0015 | 36/102 |
| 2014/0059882 | A1 * | 3/2014 | Lupinek | A43B 7/34 | 36/2.6 |

* cited by examiner

*Primary Examiner* — Timothy K Trieu
(74) *Attorney, Agent, or Firm* — Argus Intellectual Enterprise; Jordan Sworen; Daniel Enea

(57) ABSTRACT

The footwear includes a sole, a plurality of massage units, and a controller. The sole provides a support to the underside of a user's foot when the user is wearing the footwear. The massage units each include a channel, a plunger, a spring, and an actuator. The plunger is disposed within the channel and may slide within it linearly. The plunger has a shaft which terminates in an applicator, the applicator being round and configured to provide pressure to the user's foot. The spring is configured to maintain the plunger within a contact-position when at rest. This contact-position occurs when the plunger is maximally distal to the spring. The actuator is able to draw the plunger against the spring and release the plunger in repetition when energized, enacting a massaging action. The controller is able to selectively engage the actuators.

17 Claims, 5 Drawing Sheets

FOOTWEAR HAVING MULTIPLE MASSAGE DEVICES AND METHOD

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of footwear of existing art and more specifically relates to massaging footwear.

RELATED ART

To massage is to repeatedly apply pressure to the body as a therapeutic technique. Massage techniques may be done with hands, fingers, feet, other parts of the body, or a mechanical device. A massage may be applied to various parts of the body. A massage may be useful for treating physical pain, discomfort, and stress. Potential benefits for a recipient may also include reduced anxiety, depression, blood pressure, and heart rates. Some types of massage therapy have been developed to target specific combination of massage points in order to treat specific types or areas of pain.

Unfortunately, a massage usually requires a recipient to maintain a stationary position so that a massage therapist or a machine may massage the recipient. This may require devoting an unsuitable amount of time without being able to complete other tasks simultaneously. A suitable solution is desired.

U.S. Pat. No. 8,632,481 to Zheng Shi et al relates to a therapeutic shoe. The described therapeutic shoe includes a main body, a sole located at one side of the main body, a vibration layer, and a power generating module. The vibration layer is located between the main body and the sole. The power generating module includes a power generating unit, a rectifying circuit and a vibration device, which are electrically connected in series. The power generating unit generates and induces induced current.

SUMMARY OF THE INVENTION

In view of the foregoing disadvantages inherent in the known footwear art, the present disclosure provides a novel footwear having multiple massage devices and method. The general purpose of the present disclosure, which will be described subsequently in greater detail, is to provide a footwear having multiple massage devices and method.

A footwear is disclosed herein. The footwear includes a sole, a plurality of massage units, and a controller. The sole provides a support to the underside of a user's foot when the user is wearing the footwear. The massage units each include a channel, a plunger, a spring, and an actuator. The plunger is disposed within the channel and may slide within it linearly. The plunger has a shaft which terminates in an applicator, the applicator being round and configured to provide pressure to the user's foot. The spring is configured to maintain the plunger within a contact-position when at rest. This contact-position occurs when the plunger is maximally distal to the spring. The actuator is able to draw the plunger against the spring and release the plunger in repetition when energized, enacting a massaging action. The controller is able to selectively engage the actuators.

According to another embodiment, a method of selectively massaging a portion of a user's foot is also disclosed herein. The method of selectively massaging a portion of a user's foot includes providing the above-described footwear, predetermining a first-selection of massage-units chosen from the massage-units, energizing the actuators corresponding to the first-selection of massage-units, actuating the first-selection of massage-units, and optionally, predetermining additional selections of massage-units.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a footwear having multiple massage devices and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a footwear and more particularly to a footwear having multiple massage devices and method as used to improve the massaging of a foot of a user.

Generally, the footwear includes a sole with a plurality of massage-units attached to the sole. A controller may regulate operation of the massage-units. The massage-units protrude upwardly to engage a foot of a user resting on top of the sole within the footwear. Each massage unit includes a plunger riding within a channel, an actuator beneath the plunger which may retract the plunger away from the user's foot, and a coil spring separating the plunger from the actuator. The coil spring maintains the plunger in a position distal to the actuator. The plunger is limited in its travel and may not pass beyond a stop in the channel. With this structure, repeatedly energizing and deenergizing the actuator of one massage unit may cause the plunger to repeatedly reciprocate in a massaging action against the user's foot while in use. In a preferred embodiment, the controller contains a program for selecting multiples of the massage-units as desired by a user. This may be accomplished by an external device able to customize programs for the controller or may be integral to the controller and the footwear in some embodiments. This may enable a user to target specific regions of the user's foot for specific therapies and applications.

In one embodiment, the disclosure may further include a software program, particularly an application for use with a mobile device or other computing device. The program may include a user interface for programming and selecting patterns for targeting specific regions of the user's foot while using the footwear. The program may enable the computing device to be in wireless communication with the footwear such that the computing device can initiate the massaging action of the footwear in accordance with pre-programmed patterns. In particular, the user interface may provide a user with options for specified zone therapies for activating particular regions of the footwear corresponding to regions of the foot. In one example, a zone therapy program may be selected by a user to engage massage units corresponding to the innermost centers of both the left and right feet. In some therapies, this may correspond to a particular therapeutic application, such as reducing pain to the kidneys of the user of the footwear. Additional features engagable by the user interface may include selectable rates of massage unit pulsation or a constant pressure mode. Built-in programs may be based upon in-use reflexology practices, as well as customizable programs in some embodiments. The software program may also include tutorials and other educational features.

Referring now more specifically to the drawings by numerals of reference, there is shown in FIGS. 1-4, various views of a footwear 100.

Figure 1:
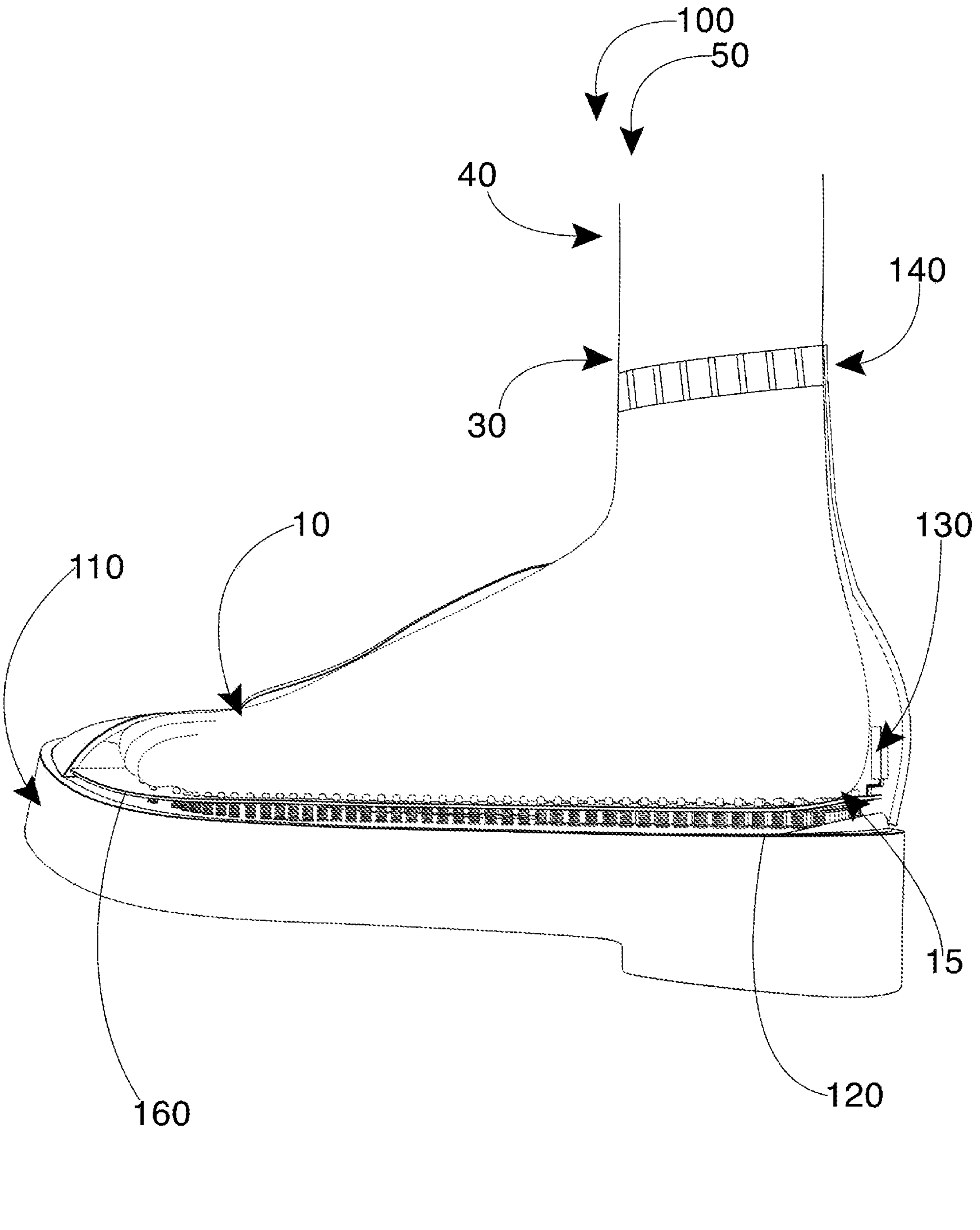
FIG. 1 is a cutaway view of the footwear during an 'in-use' condition, according to an embodiment of the disclosure.

FIG. 1 shows a footwear during an 'in-use' condition 50, according to an embodiment of the present disclosure. Here, footwear 100 may be beneficial for use by a user 40 to selectively massage a portion of a foot of a user. As illustrated, footwear 100 may include sole 110, insole 160, plurality of massage-units 120, controller 130, and cuff 140. Footwear 100 may be able to massage foot 10 of user 40. Sole 110 may be configured to support underside 15 of foot 10 of user 40, with plurality of massage-units 120 being embedded within sole 110. Insole 160 may be disposed on top of sole 110, such that insole 160 provides cushioning between foot 10 and sole 110. Insole 160 may be malleable and may be configured to cushion foot 10 of user 40 against plurality of massage-units 120. Thereby, plurality of massage-units 120 may be able to provide pressure via a massaging action to foot 10 through displacement of insole 160. In alternative embodiments, plurality of massage-units 120 may pass through insole 160. Controller 130 may be in electrical communication with plurality of massage-units 120 and may be configured to selectively engage one or more of plurality of massage-units 120. Preferably, footwear 100 is a boot as shown.

Figure 2:
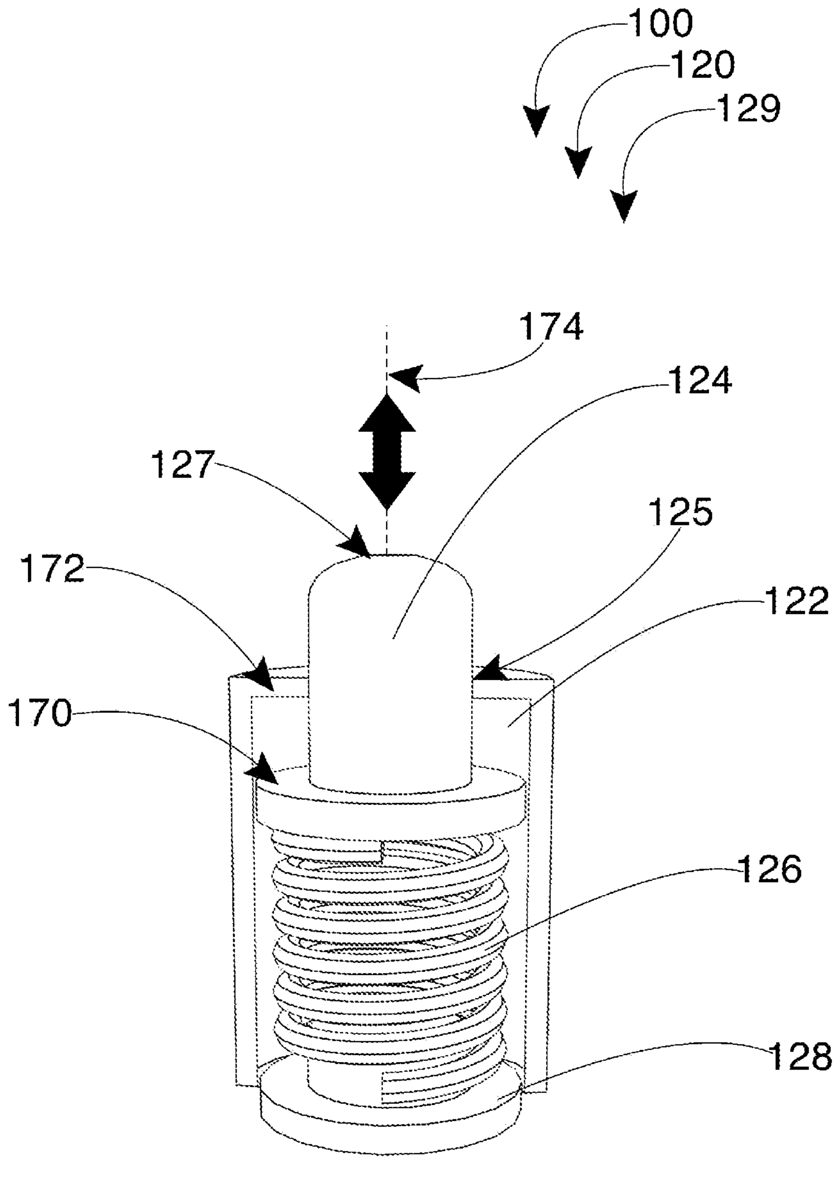
FIG. 2 is a perspective view of the plurality of massage-units of the footwear of FIG. 1, according to an embodiment of the present disclosure.

FIG. 2 shows footwear 100 of FIG. 1, according to an embodiment of the present disclosure. As above, footwear 100 may include plurality of massage-units 120. Each of plurality of massage-units 120 may include channel 122, plunger 124, spring 126, and actuator 128. Plunger 124 may be configured to slide within channel 122 and may have shaft 125 terminating in applicator 127. Applicator 127 may be round in a preferred embodiment and may be configured to provide pressure to foot 10 (FIG. 1) when actuator 128 is energized. In alternative embodiments applicator 127 may be flat or have other contours. Spring 126 may be configured to maintain plunger 124 in contact-position 129, such that contact-position 129 may be distal to spring 126. Spring 126 may be a coil spring able to be compressed between plunger 124 and actuator 128. Actuator 128 may be configured to draw plunger 124 against spring 126 and release plunger 124 in repetition, thereby effecting a massaging action when foot 10 (FIG. 1) is placed against plurality of massage-units 120 and alternatively insole 160 (FIG. 1). Channel 122 of each of plurality of massage-units 120 is characterized by channel-axis 174, channel 122 being a cylinder, such that channel 122-axis passes through the center of channel 122. Preferably, channel 122 and plunger 124 are each cylindrical, such that plunger 124 is nested within channel 122 may only travel linearly within channel 122 along channel-axis 174. Plunger 124 of the massage unit may further include flange 170. Channel 122 of the massage unit may also further include constriction 172. Flange 170 may be annular and concentric to plunger 124, while constriction 172 may likewise be annular and concentric to channel 122. Flange 170 may be structured and arranged to impinge upon constriction 172, having dimensions that prevent flange 170 from passing beyond constriction 172, thereby retaining plunger 124 within channel 122. Flange 170 may be configured to prevent plunger 124 from leaving channel 122 despite forces being enacted upon plunger 124 by spring 126 and actuator 128. Preferably, actuator 128 is an electromagnet configured to draw plunger 124 against spring 126 when energized. Channel 122, plunger 124, spring 126, and actuator 128 may all be cylindrically shaped and may each be arranged concentrically to one another.

Figure 3:
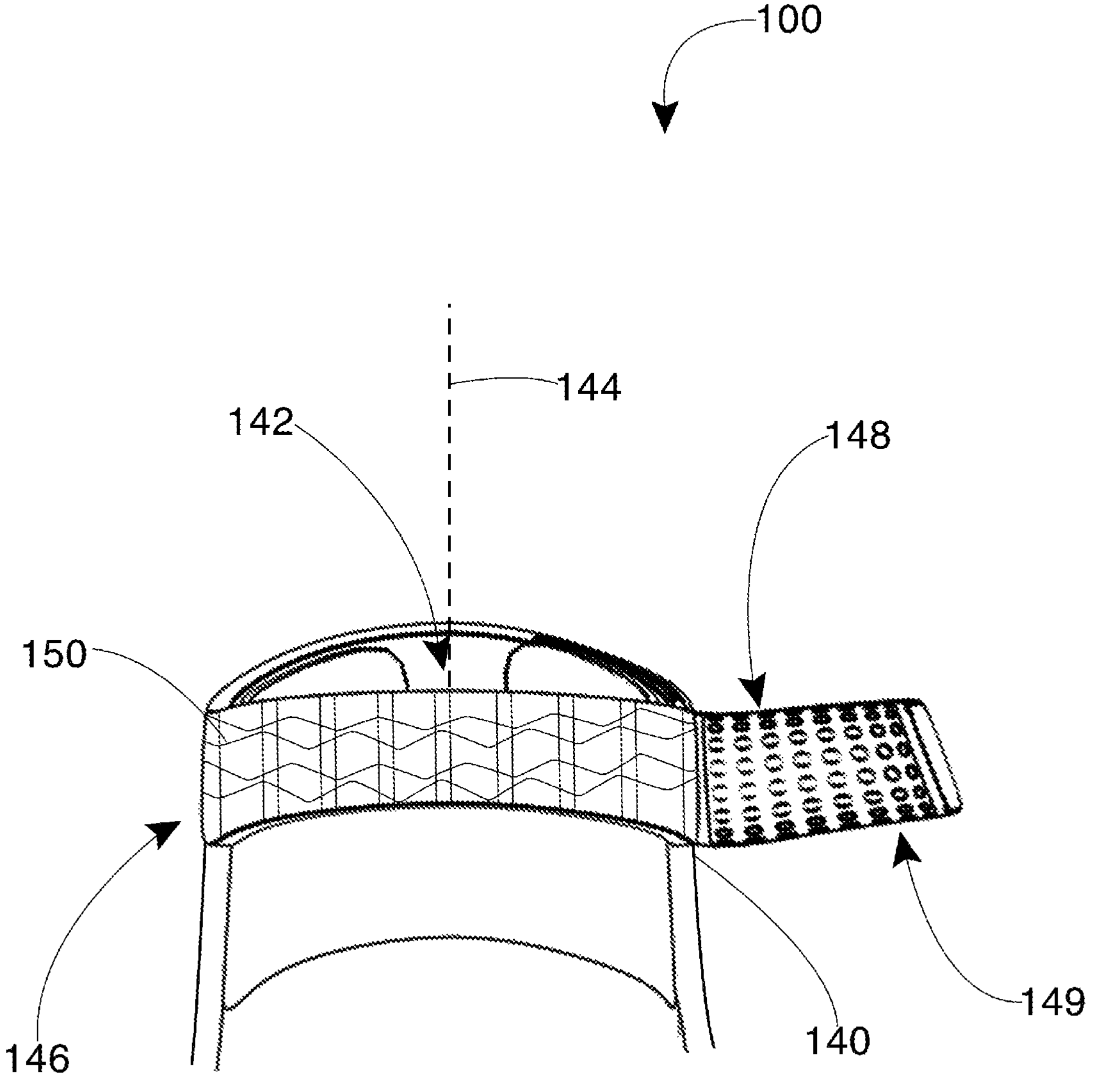
FIG. 3 is a perspective view of the footwear of FIG. 1, according to an embodiment of the present disclosure.

FIG. 3 is a perspective view of footwear 100 of FIG. 1, according to an embodiment of the present disclosure. Cuff 140 may itself include aperture 142. Aperture 142 may be sufficiently large for ankle 30 (FIG. 1) of user 40 (FIG. 1) to pass through aperture 142. Cuff-axis 144 may pass centrally through aperture 142. Cuff-axis 144 may be disposed approximately parallel to cylinder-axis 174 (FIG. 2). Footwear 100 may further include electric resistance heater 150. Electric resistance heater 150 may be configured to produce heat when energized and may be disposed within cuff 140 of footwear 100. In one embodiment, cuff 140 of footwear 100 may be elastic. In another embodiment, cuff 140 of footwear 100 may include exterior 146, strap 148, and hook-and-loop fastener 149. Hook-and-loop fastener 149 may be configured to affix strap 148 to exterior 146, such that strap 148 may circumscribe cuff 140, and may constrict cuff 140 about ankle 30 (FIG. 1) of user 40 (FIG. 1) when hook-and-loop fastener 149 is engaged.

Figure 4:
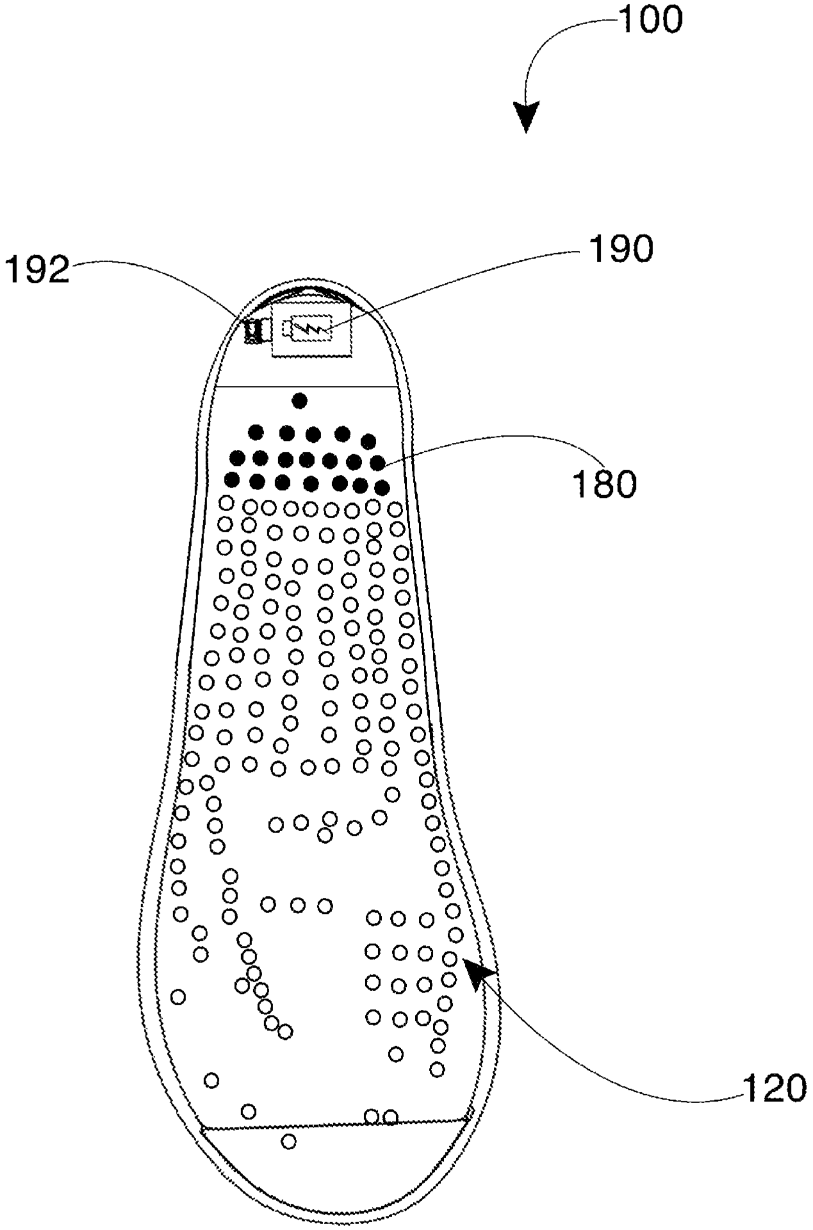
FIG. 4 is a cutaway view of the footwear of FIG. 1, according to an embodiment of the present disclosure.

FIG. 4 is a perspective view of footwear 100 of FIG. 1, according to an embodiment of the present disclosure. Plurality of massage units 120 may be in electrical communication with power source 190, switching means 192, and controller 130 (FIG. 1). Power source 190 may be able to selectively engage each of plurality of massage-units 120 independently via controller 130 (FIG. 1). In this way, a specific combination of plurality of massage-units 120 may be engaged in order to target and massage a particular area of the foot as desired by user 40 (FIG. 1). In one embodiment, controller 130 (FIG. 1) is programmable, such that user 40 (FIG. 1) may select customizable combination 180 of the plurality of massage units 120 to energize while in use. Power source 190 may be in electric communication with controller 130 and each of actuators 128 (FIG. 2) in combination, such that the power source 190 may selectively engage each of actuators 128 (FIG. 2) independently via controller 130. Preferably, power source 190 is a battery. Switching means 192 may enable user 40 (FIG. 1) to selectively connect the power source 190 to plurality of massage-units 120 manually.

Upon reading this specification, it should be appreciated that, under appropriate circumstances, considering such issues as user preferences, design preference, structural requirements, marketing preferences, cost, available materials, technological advances, etc., other structural arrangements such as, for example, different footwear structures, additional massage features, alternative arrangements of massage devices, etc., may be sufficient.

Figure 5:
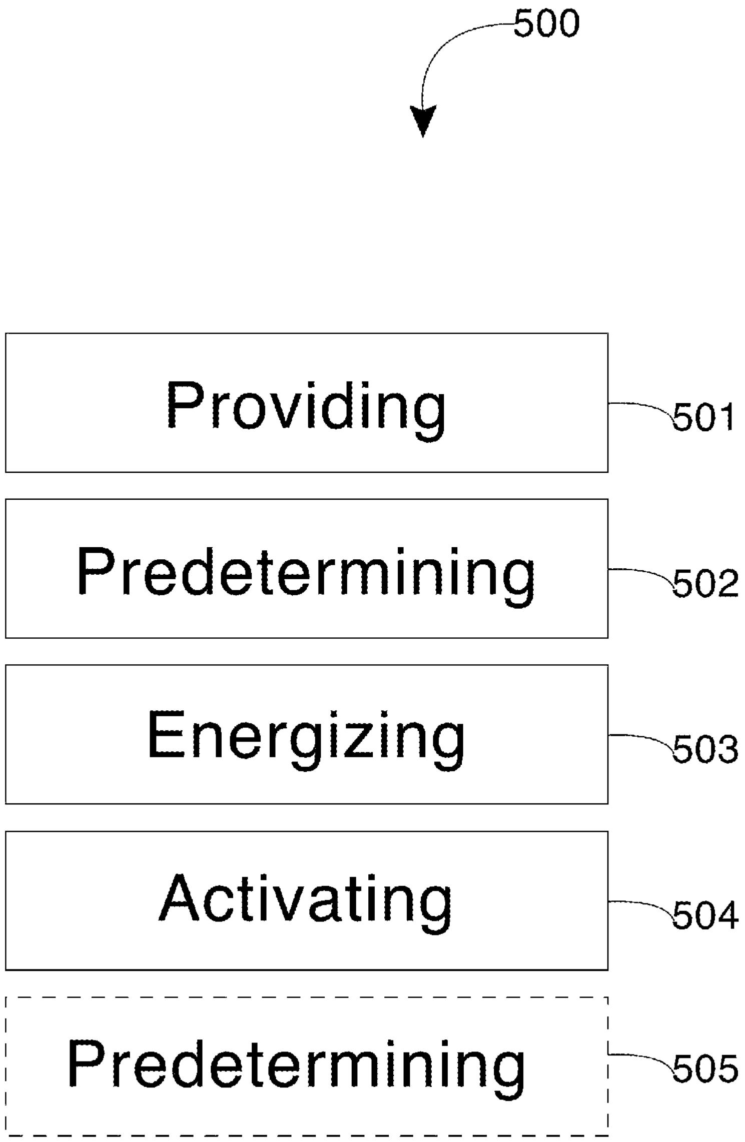
FIG. 5 is a flow diagram illustrating a method of use for selectively massaging a portion of a foot of a user, according to an embodiment of the present disclosure.

FIG. 5 is a flow diagram illustrating a method for selectively massaging a portion of a foot of a user, according to an embodiment of the present disclosure. In particular, the method for selectively massaging a portion of a foot of a user 500 may include one or more components or features of the footwear 100 as described above. As illustrated, the method for selectively massaging a portion of a foot of a user 500 may include the steps of: step one 501, providing a footwear able to massage a foot of a user, the footwear comprising: a sole configured to support an underside of the foot of the user; a plurality of massage-units each including a channel, a plunger, the plunger being configured to slide within the channel, the plunger having a shaft terminating in an applicator, the applicator being round, a spring configured to maintain the plunger in a contact-position, the contact-position being distal to the spring, an actuator configured to draw the plunger against the spring and release the plunger in repetition; and a controller configured to selectively engage the actuators; step two 502, predetermining a first-selection of massage-units chosen from the plurality of massage-units; step three 503, energizing the actuators corresponding to the first-selection of massage-units; step four 504, actuating the first-selection of massage-units; and step five 505, predetermining a second-selection of massage-units chosen from the plurality of massage-units.

It should be noted that step 505 is an optional step and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for selectively massaging a portion of a foot of a user, are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A footwear able to massage a foot of a user, the footwear comprising:

a sole configured to support an underside of the foot of the user;

a plurality of massage-units each including a channel, a plunger, the plunger being configured to slide within the channel, the plunger having a shaft terminating in an applicator, the applicator being round, a spring configured to maintain the plunger in a contact-position, the contact-position being distal to the spring, and an actuator configured to draw the plunger against the spring and release the plunger in repetition; and a controller configured to selectively engage the actuators;

a software program, the software program being installable on a computing device, such that the software program enables the computing device to be in wireless communication with the footwear.

2. The footwear of claim 1, wherein the channel and the plunger are each cylindrical.

3. The footwear of claim 2, wherein the plunger of the massage unit further includes a flange and the channel of the massage unit further includes a constriction, the flange being annular and concentric to the plunger, the constriction being annular and concentric to the channel, the flange being structured and arranged to impinge upon the constriction, the flange being configured to prevent the plunger from leaving the channel.

4. The footwear of claim 1, further comprising a cuff, the cuff having an aperture sufficiently large for an ankle of the user to pass through, and a cuff-axis passing centrally through the aperture.

5. The footwear of claim 4, further comprising an electric resistance heater configured to produce heat when energized, the electric resistance heater being disposed within the cuff of the footwear.

6. The footwear of claim 4, wherein the cuff of the footwear is elastic.

7. The footwear of claim 4, wherein the cuff of the footwear includes an exterior, a strap, and a hook-and-loop fastener configured to affix the strap to the exterior, such that the strap circumscribe the cuff, and constricts the cuff about an ankle of the user when the hook-and-loop fastener is engaged.

8. The footwear of claim 1, wherein the actuator is an electromagnet configured to draw the plunger against the spring when energized.

9. The footwear of claim 1, wherein the footwear is a boot.

10. The footwear of claim 1, wherein the controller is programmable, such that the user may select a combination of the plurality of massage-units to energize while in use.

11. The footwear of claim 1, further comprising a power source in electric communication with the controller and each of the actuators, such that the power source may selectively engage each of the actuators independently via the controller.

12. The footwear of claim 11, wherein the power source is a battery.

13. The footwear of claim 11, further comprising a switching means for selectively connecting the power source to the actuator.

14. The footwear of claim 1, wherein each channel of each of the plurality of massage-units is characterized by a channel-axis, the channel being a cylinder, such that the channel-axis passes through the center of the cylinder, the channel-axis being parallel to the cuff-axis.

15. The footwear of claim 1, wherein the spring is a coil spring, the coil spring being compressed between the plunger and the actuator.

16. The footwear of claim 1, further comprising an insole, the insole being malleable, the insole being configured to cushion the foot of the user against the plurality of massage-units.

17. A footwear able to massage a foot of a user, the footwear comprising:

a sole configured to support an underside of the foot of the user;

a plurality of massage-units each including a channel, a plunger, the plunger being configured to slide within the channel, the plunger having a shaft terminating in an applicator, the applicator being round, a spring configured to maintain the plunger in a contact-position, the contact-position being distal to the spring, and an actuator configured to draw the plunger against the spring and release the plunger in repetition; and a controller configured to selectively engage the actuators;

wherein the channel and the plunger are each cylindrical;

further comprising a cuff, the cuff having an aperture sufficiently large for an ankle of the user to pass through, and a cuff-axis passing centrally through the aperture further comprising an electric resistance heater configured to produce heat when energized, the electric resistance heater being disposed within the cuff of the footwear;

wherein the actuator is an electromagnet configured to draw the plunger against the spring when energized;

wherein the plunger of the massage unit further includes a flange and the channel of the massage unit further includes a constriction, the flange being annular and concentric to the plunger, the constriction being annular and concentric to the channel, the flange being structured and arranged to impinge upon the constriction, the flange being configured to prevent the plunger from leaving the channel;

wherein the footwear is a boot;

wherein the controller is programmable, such that the user may select a combination of the plurality of massage-units to energize while in use;

further comprising a power source in electric communication with the controller and each of the actuators, such that the power source may selectively engage each of the actuators independently via the controller;

wherein the power source is a battery further comprising a switching means for selectively connecting the power source to the actuator;

wherein each channel of each of the plurality of massage-units is characterized by a channel-axis, the channel being a cylinder, such that the channel-axis passes through the center of the cylinder, the channel-axis being parallel to the cuff-axis;

wherein the spring is a coil spring, the coil spring being compressed between the plunger and the actuator; and further comprising an insole, the insole being malleable, the insole being configured to cushion the foot of the user against the plurality of massage-units.

* * * * *